US010912877B2

(12) United States Patent
Fabig et al.

(10) Patent No.: US 10,912,877 B2
(45) Date of Patent: Feb. 9, 2021

(54) APPARATUS FOR THE EXTRACORPOREAL REMOVAL OF PROTEIN-BOUND TOXINS

(71) Applicant: FRESENIUS MEDICAL CARE DEUTSCHLAND GMBH, Bad Homburg (DE)

(72) Inventors: Anselm Fabig, Zeuthen (DE); Ulrich Tschulena, Frankfurt am Main (DE); Sonja Steppan, Neu-Isenburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 872 days.

(21) Appl. No.: 15/328,326

(22) PCT Filed: Jul. 20, 2015

(86) PCT No.: PCT/EP2015/001499
§ 371 (c)(1),
(2) Date: Jan. 23, 2017

(87) PCT Pub. No.: WO2016/012093
PCT Pub. Date: Jan. 28, 2016

(65) Prior Publication Data
US 2017/0216513 A1    Aug. 3, 2017

(30) Foreign Application Priority Data
Jul. 23, 2014   (DE) .......................... 10 2014 010 907

(51) Int. Cl.
*A61M 1/36*   (2006.01)
*A61M 1/16*   (2006.01)
*A61M 1/34*   (2006.01)

(52) U.S. Cl.
CPC ............ *A61M 1/3681* (2013.01); *A61M 1/16* (2013.01); *A61M 1/3472* (2013.01); *A61M 2205/054* (2013.01)

(58) Field of Classification Search
None
See application file for complete search history.

(56) References Cited

U.S. PATENT DOCUMENTS 3,827,961 A      8/1974  Doniat et al.
4,505,275 A  *   3/1985  Chen .................. A61N 1/36021
                                              607/62
(Continued)

FOREIGN PATENT DOCUMENTS

CN       2810611         8/2006
CN       2438454         7/2011
(Continued)

OTHER PUBLICATIONS

Yaduvir Singh, Electromagnetic Field Theory 178 (2011). (Year: 2011).*

*Primary Examiner* — Krishnan S Menon
*Assistant Examiner* — Brad Gordon
(74) *Attorney, Agent, or Firm* — Jacobson Holman PLLC

(57) ABSTRACT

The present invention relates to an apparatus for the extracorporeal removal of protein-bound toxins from blood comprising at least one blood purification apparatus, in particular at least one dialysis machine, hemofilter or adsorber, as well as at least one means for generating a field in the blood purification apparatus and/or in an element in flow communication with the blood purification apparatus, in particular in a line section connected to the blood purification apparatus, wherein the means comprises at least two strip conductors which are arranged on at least two preferably oppositely disposed sides of the blood purification apparatus or of the element such that the field is preferably predomi- (Continued)

Figure 1:
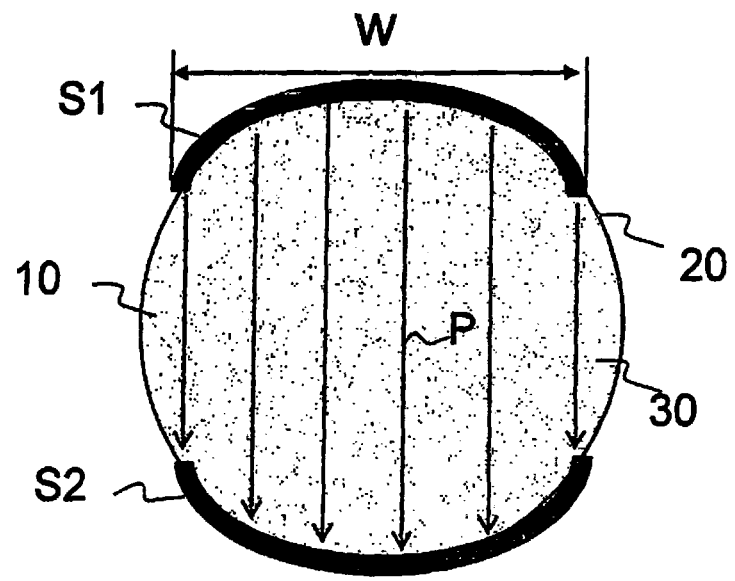

nantly generated within the blood purification apparatus or preferably predominantly within the element.

13 Claims, 3 Drawing Sheets

(56) References Cited

U.S. PATENT DOCUMENTS

| | | | | |
|---|---|---|---|---|
| 4,888,109 | A * | 12/1989 | Manohar | B01D 63/02 210/94 |
| 5,188,738 | A * | 2/1993 | Kaali | A61L 2/0011 204/164 |
| 2004/0193000 | A1 * | 9/2004 | Riehl | A61N 2/006 600/9 |
| 2006/0122454 | A1 * | 6/2006 | Riehl | A61N 2/008 600/9 |
| 2006/0196817 | A1 * | 9/2006 | Crewson | C02F 1/48 210/223 |
| 2006/0282122 | A1 * | 12/2006 | Palti | A61N 1/40 607/2 |
| 2007/0038156 | A1 * | 2/2007 | Rosenberg | A61B 18/14 601/2 |
| 2007/0255085 | A1 * | 11/2007 | Kishawi | A61N 7/00 600/9 |
| 2010/0312233 | A1 * | 12/2010 | Furnish | A61N 1/40 606/33 |
| 2011/0262300 | A1 * | 10/2011 | Rahn | A61L 2/0035 422/22 |
| 2015/0306298 | A1 * | 10/2015 | Tschulena | A61M 1/3618 210/143 |

FOREIGN PATENT DOCUMENTS

| | | |
|---|---|---|
| CN | 103402563 | 11/2013 |
| CN | 103751868 | 4/2014 |
| EP | 2092944 | 7/2012 |
| WO | WO 2014/095072 | 6/2014 |

* cited by examiner

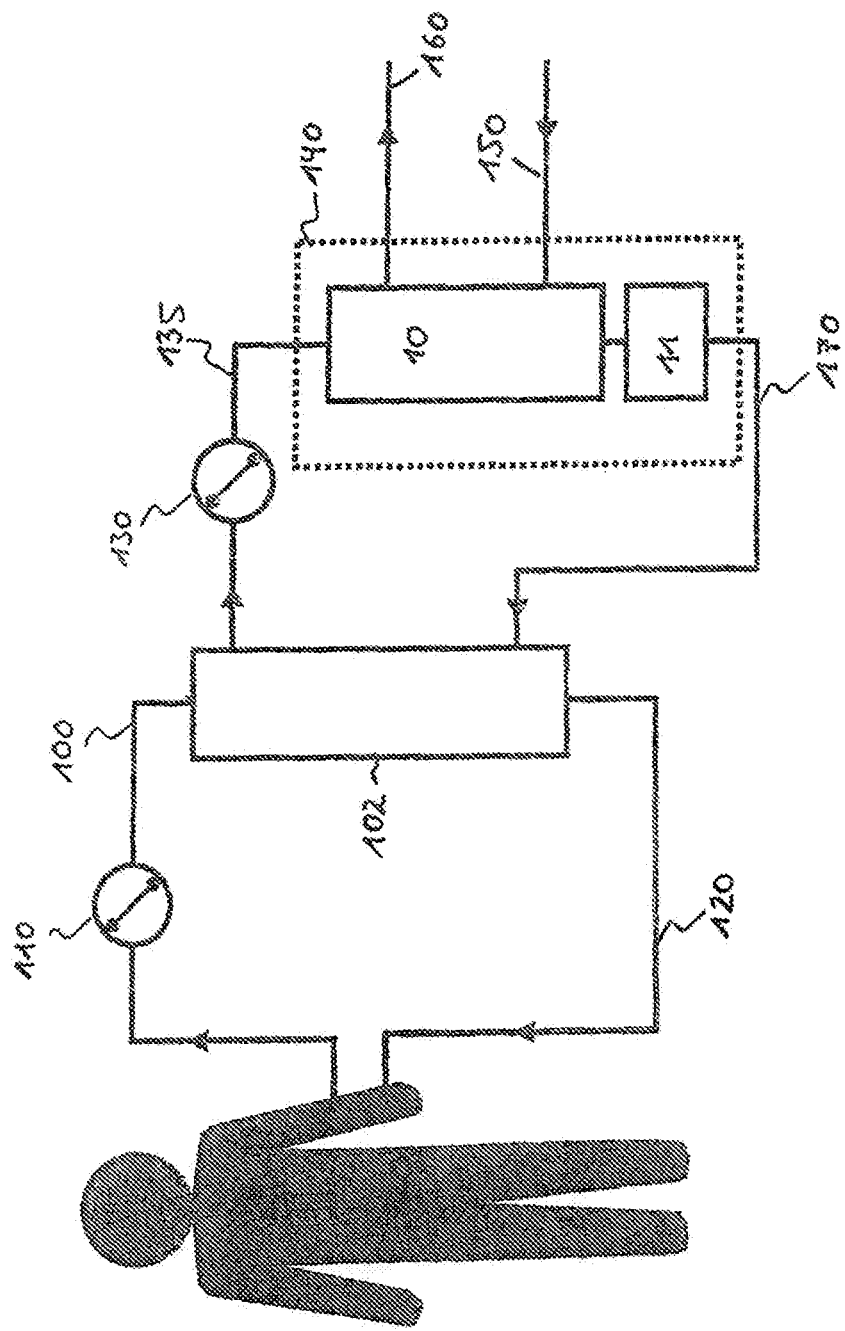

APPARATUS FOR THE EXTRACORPOREAL REMOVAL OF PROTEIN-BOUND TOXINS

The present invention relates to an apparatus for the extracorporeal removal of protein-bound toxins from blood comprising at least one blood purification apparatus, in particular at least one dialysis machine, hemofilter or adsorber, as well as at least one means for generating a field in the blood purification apparatus and/or in an element in flow communication with the blood purification apparatus, which element is preferably at least one line section connected to the blood purification apparatus.

In healthy persons, different substances dissolved in the blood such as uremic toxins are excreted via the kidney together with the urine. In the event of renal failure or if the kidneys can no longer satisfy this purification function or can only satisfy it with limitations, the substances in question have to be removed from the blood by means of a blood purifications process such as by means of hemodialysis or peritoneal dialysis.

Water-soluble toxins such as urea cannot easily be removed from the blood using the known blood purifications processes. In contrast, the removal of poorly water soluble hydrophobic uremic toxins by means of the known blood purification processes is made more difficult due to the protein binding of these toxins.

Plasma proteins, in particular albumin which is retained by typical dialysis membranes due to its size, can be considered as binding partners for uremic toxins. This applies accordingly to uremic toxins which enter into a bond with albumin. There is admittedly a balance between the free uremic toxins and the protein-bound uremic toxins which has the result that, with a sufficiently long blood treatment, a substantial portion of the uremic toxins is removed by means of the blood purification apparatus, but such a long time period is typically not available for the treatment.

An apparatus is known from WO 2014/095072 A1 which comprises means for generating an electromagnetic field which has an effect on the blood. The background for this procedure is that the strength of the bindings or the interactions between the uremic toxins and the proteins is reduced by the effect of the field, whereby the proportion of the protein-bound uremic toxins can be considerably reduced. Consequently, an improved separation of the uremic toxins from the blood of a patient can be achieved in the blood purification. Capacitors are, for example, used for generating the field.

It is the underlying object of the present invention to further develop an apparatus of the initially named kind such that the efficiency of the separation of the uremic toxins from the plasma proteins is improved with respect to the known apparatus.

This object is achieved by an apparatus having the features described below.

Provision is accordingly made that the means comprises at least two strip conductors which are arranged at the blood purification apparatus or at the element such that the field, in particular an electromagnetic field, spreads within the blood purification apparatus and/or within the element. The field thus spreads at least partially and preferably predominantly within the blood purification apparatus or within the element, which also includes the case that the field only spreads within the blood purification apparatus or within the element.

The named element can, for example, be a line or a line section or another component through which the blood or a portion thereof flows from said element to the blood purification apparatus.

The arrangement of the strip conductors on the blood purification apparatus or on the named element has the advantage that the field extends completely or largely through the blood purification apparatus, such as through a dialysis machine, or through the named element and thus particularly efficiently effects the separation of the existing bonds between plasma proteins, in particular albumin, and uremic toxins in the blood.

A further advantage of the arrangement is that the field preferably predominantly spreads within the blood purification apparatus. Since the $\varepsilon_r$ of air is approximately equal to 1, and is thus very much smaller than the $\varepsilon_r$ of water or blood, only a smaller portion of the field is irradiated into the surrounding air. This has the advantage that lower demands are made on the screening of the blood purification apparatus and under certain circumstances a screening at all sides can be completely dispensed with.

The strip conductors are preferably arranged on the outer side of the blood purification apparatus or of the element and preferably directly or indirectly on the outer side of the housing of the blood purification apparatus or of the element.

Provision is made in a preferred embodiment of the invention that the strip conductors are connected to the blood purification apparatus or to the element such that no air is located between the strip conductors and the blood purification apparatus or the element. An air-free connection of the strip conductors to the blood purification apparatus or to the element is thus preferred.

The strip conductors are arranged, for example, such that they extend on two oppositely disposed sides of the blood purification or of the element and preferably symmetrically to a longitudinal plane of the blood purification apparatus or of the element.

The means can comprise two or also more than two strip conductors.

The strip conductors can, for example, be adhesively bonded to the blood purification apparatus or to the element or can be mechanically fastened to the blood purification apparatus or to the element, e.g. by one or more clamps, etc.

Provision can be made to achieve a good, air-free connection of the strip conductors to the blood purification apparatus or to the element that an aqueous gel is located between the strip conductors and the blood purification apparatus or the element. A gel can be considered such as is used in ultrasound applications.

The means for generating a field can be configured such that an electromagnetic field is generated having a frequency in the range from 1 MHz to 1 GHz, and preferably having a frequency in the range from 60 MHz to 200 MHz, and particularly preferably having a frequency in the range from 100 MHz to 120 MHz.

A frequency in the range from 110 MHz to 111 MHz has proved particularly suitable.

Provision can furthermore be made that the means for generating a field is configured such that the field has a field strength in the range of up to 4000 V/m, preferably in the range from 2000 V/m to 4000 V/m, and particularly preferably in the range from 3000 V/m to 3200 V/m.

The field generated by the strip conductors can be a radio-frequency electromagnetic field having a superimposed static electric field.

The blood purification apparatus or the element can have a curved surface at least regionally. It is thus conceivable, for example, that the blood purification apparatus is a dialysis machine having a cylindrical housing and/or that the element is a component such as a hose, a pipe, etc. having a curved wall. The strip conductors can likewise be curved so that they follow the contour of the surface of the blood purification apparatus or of the element.

As stated above, it is conceivable that the strip conductors are adhesively bonded to the outer side of the housing of the blood purification apparatus or of the element or are otherwise fixed there and thus likewise have a curvature in the case of a curved surface.

The case is naturally also covered by the invention that the blood purification apparatus or the element has a planar surface and the strip conductors are thus likewise planar.

It is conceivable that the strip conductors are partly or completely configured as a film or as a plate-shaped element or as elements or holders partly or completely engaging around the blood purification apparatus or the element.

The strip conductors preferably partly or completely comprise metal. The use of copper or aluminum is preferably provided.

It is conceivable that the strip conductors extend over the total length of the blood purification apparatus or of the element or over a part of the total length, preferably over more than half the length, of the blood purification apparatus or of the element. If the blood purification apparatus or the named element, for example, has an elongate form, provision can be made that the strip conductors extend over the total length or at least over a predominant part of the length of the blood purification apparatus or of the element.

Provision is preferably made that the strip conductors are dimensioned such that the field generated by them passes through the total space in which the blood is located or through a predominant part of this space.

The apparatus preferably has at least one extracorporeal circuit in which the blood purification apparatus and/or the named element is/are located.

As stated above, the blood purification apparatus can, for example, be a dialysis machine or a hemofilter which is used in a hemofiltration treatment or in hemodiafiltration. Alternatively or additionally, the blood purification apparatus can also be an adsorber or the like with which specific substances are removed from the blood by adsorption.

The adsorber can be an anion exchanger or a hydrophobic adsorber, for example activated carbon, which preferably has a hemocompatible coating. It holds back toxins and in this manner prevents them from being supplied back to the patient.

Provision can furthermore be made that the extracorporeal circuit comprises at least one filter which is connected to a permeate side and to a retentate side, with the blood purification apparatus being connected to the permeate side. A cell separator can also be used which separates the blood into blood plasma and into a cellular component, with the cell separator being connected such that the blood plasma, but not the cellular components of the blood, enter into the blood purification apparatus.

The apparatus in accordance with the invention can be used in the treatment of acute or chronic renal failure.

The apparatus in accordance with the invention can also be used in the treatment of acute or chronic liver failure.

The apparatus in accordance with the invention can also be used in the treatment of patients having sepsis or be used in the treatment of patients having toxication in an apparatus for detoxication of patients.

Further details and advantages of the invention will be explained in more detail with reference to an embodiment shown in the drawing.

Figure 2:
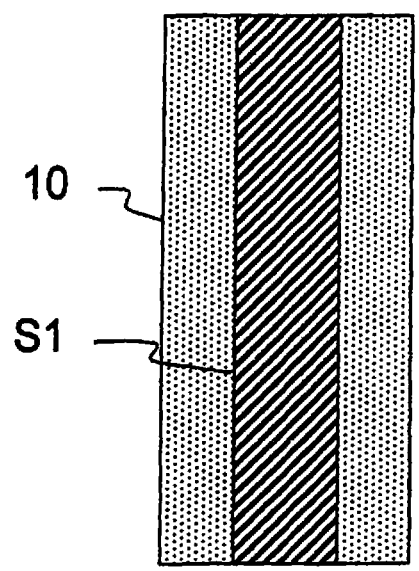
Figure 3:
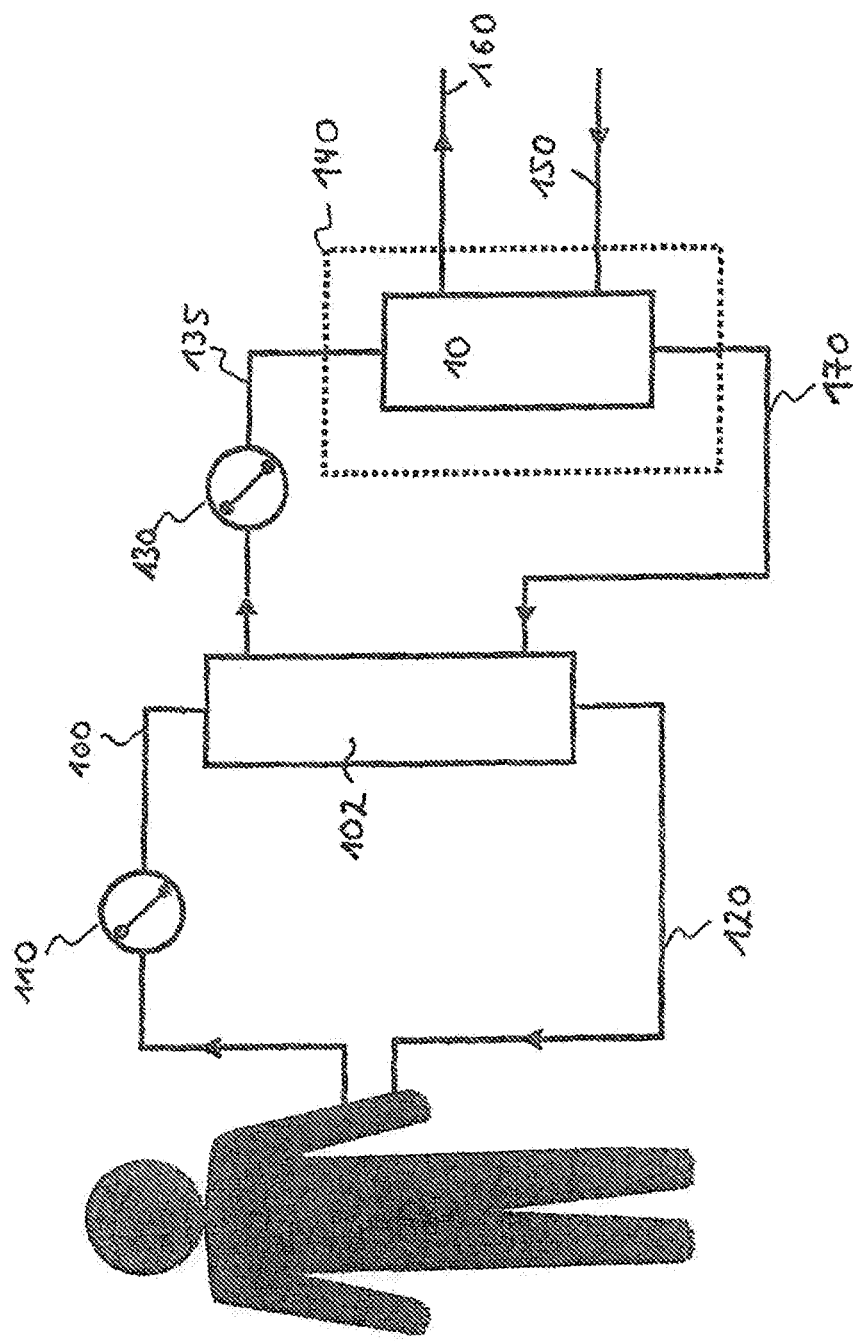

There are shown:

FIG. 1: a schematic cross-sectional view through a dialysis machine with strip conductors arranged on oppositely disposed sides;

FIG. 2: a detailed view of a section of the dialysis machine with a strip conductor arranged on its outer side;

FIG. 3: a schematic view of an apparatus in accordance with the invention with a plasma filter and a dialysis machine; and FIG. 4: a schematic view of an apparatus in accordance with the invention with a plasma filter and a dialysis machine as well as an adsorber.

FIG. 1 shows in a schematic cross-sectional view a dialysis machine 10 which has a cylindrical housing 20 in whose inner space 30 a fiber bundle, not shown, is located. In the treatment, the fibers of the fiber bundle are flowed through by blood; the region surrounding the fiber bundle is flowed around by the dialysis solution.

The blood purification takes place by diffusion over the walls of the fibers configured as membranes.

Every other blood purification apparatus is equally covered by the invention such as a hemofilter in which a mass transfer takes place over the fiber membranes due to a pressure gradient or also a hemodiafilter in which the blood purification takes place over the fiber membranes both due to a concentration gradient and due to a pressure gradient. Other blood purification apparatus, such as an adsorber, are also covered by the invention.

As can furthermore be seen from FIG. 1, strip conductors S1 and S2, which are curved in accordance with the curvature of the dialysis machine housing, as can be seen from FIG. 1, are located arranged symmetrically relative to a center plane through the dialysis machine 10 extending perpendicular to the plane of the paper. The strip conductors are acted on by current/voltage such that a field forms between them which is located within the dialysis machine.

The arrows P in FIG. 1 mark a field which extends between strip conductors and which is preferably an electromagnetic field, and particularly preferably a radio-frequency electromagnetic field.

The width W of the strip conductors S1 and S2 in FIG. 1 is selected such that a wave resistance of 50Ω is produced.

If a diameter of the dialysis machine 10 of 32 mm is assumed, a field of 3125 V/m can be achieved on a use of a 200 W amplifier at 50Ω and at a frequency in the range from 110-111 MHz.

In the arrangement shown in FIG. 1, the strip conductors are airtight, i.e. are connected without an air cushion or air inclusions directly or indirectly to the outer side of the dialysis machine housing. The connection can take place by adhesive bonding, by mechanical means, etc.

It can be further seen from FIG. 1 that the strip conductors extend on oppositely disposed sides of the dialysis machine. They each engage around a part region of the dialysis machine; further part regions of the dialysis machine periphery are not provided with strip conductors, as can be seen from FIG. 1.

A view of a part region of the dialysis machine 10 can be seen from FIG. 2. A copper film is applied to the outer surface of the dialysis machine; it serves as strip conductors S1, S2 and extends in the direction of the longitudinal extent of the dialysis machine 10.

The arrangement of the strip conductor in direct connection to the dialysis machine or to another blood purification apparatus brings about the advantage that a high field strength can be achieved within the blood purification apparatus and accordingly a particularly effective separation of the uremic toxins from their binding partners, in particular from proteins, can take place. This in turn allows the efficient separation of the toxins from the blood, for example by means of a dialysis machine.

FIG. 3 shows a conceivable embodiment of an arrangement for blood purification.

Reference numeral 100 marks a line by means of which blood is conducted from a patient access to the plasma filter 102. The pump 10 serves the conveying of the blood. The retentate of the plasma filter 102 and the blood purified in the dialysis machine 10 is supplied back to the patient via the line 120.

A separation of the blood into cellular components and into plasma takes place in the plasma filter 102, with the cellular components being retained and the plasma passing through the filter membrane.

The blood plasma acquired in the plasma filter 102 is supplied by means of the pump 130 via the line 135 to the dialysis machine 10.

Reference numeral 140 symbolically marks the strip conductors S1, S2 arranged on the dialysis machine 10 which generate a field, and preferably a radio-frequency electromagnetic field, within the dialysis machine 10.

As stated above, the field effects a separation of the uremic toxins from proteins, in particular from albumin, so that the proportion of free uremic toxics can be increased accordingly. They can be conducted away via the membrane of the dialysis machine 10 and can be received by a dialysis solution which flows around the hollow fibers of the dialysis machine 10 and which is conducted to or from the dialysis machine by means of the lines 150, 160.

The blood purified in the dialysis machine 10 is supplied via the line 170 to the plasma filter 102 and is there mixed with the cellular components which were retained by the filter membrane of the plasma filter 102 and is again supplied to the patient via the line 120.

The arrangement of a plasma filter before the dialysis machine or before another blood purification apparatus brings along the advantage that the cellular components are not exposed to the electromagnetic field in the dialysis machine, whereby the biocompatibility of the process is increased.

FIG. 4 shows a further embodiment of an arrangement for blood purification, with the same reference numerals as in FIG. 3 showing identical components or components of the same function.

As can be seen from FIG. 4, not only a dialysis machine 10 is provided as a blood purification apparatus, but also additionally an adsorber 11, which can be arranged before or after the dialysis machine 10. The adsorber can likewise be provided with strip conductors so that there is also a field in the adsorber.

The adsorber has the function of adsorbing, and thus removing from the blood circuit, toxins which are released in the field and which are not separated via the dialysis machine membrane.

The strip conductors are arranged both at the dialysis machine 10 and at the adsorber 11 in the embodiment shown in FIG. 4.

An embodiment is also covered by the invention in which e.g. only the dialysis machine or only the adsorber is provided with strip conductors.

An embodiment is, for example, conceivable in which the adsorber provided with strip conductors is connected upstream of the dialysis machine. In this case, a release of toxins which can be separated in the dialysis machine takes place in the adsorber.

The embodiment relates to the arrangement of the strip conductors at a dialysis machine. However, the arrangement of the strip conductors at any other desired blood purification apparatus as well as at other components, in particular lines, is also covered by the invention and by the embodiment. They are preferably located in an extracorporeal circuit in which the blood of a patient or a component, in particular the blood plasma, is subjected to a purification.

The invention claimed is:

1. An apparatus for the extracorporeal removal of protein-bound toxins from blood comprising
    at least one blood purification apparatus selected from the group consisting of a dialysis machine, a hemofilter, and an adsorber, wherein each of said dialysis machine, hemofilter, and adsorber have, respectively, an outer side comprising a first side and a second side, such that the first side is opposite the second side,
    an element in flow communication with the at least one blood purification apparatus, wherein the element is a line section connected to the at least one blood purification apparatus, wherein said element has an outer side comprising a first side and a second side, such that the first side of the element is opposite the second side of the element,
    at least one means for generating a field configured to generate a field in one or more of the element and the at least one blood purification apparatus, such that the field is predominantly generated within at least one of the at least one blood purification apparatus and the element characterized in that each of the means comprises at least two strip conductors arranged on either the outer side of one of the element or the outer side of the at least one blood purification apparatus such that at least one of the at least two strip conductors is on the first side of the outer side and at least one of the at least two strip conductors in on the second side of the outer side,
    wherein, for each strip conductor, an aqueous gel is located between said strip conductor and the outer side on which it resides such that no air is located between the strip conductor and the outer side, and
    wherein the field is an electromagnetic field and also wherein the field is configured to separate uremic toxins from proteins so that a proportion of free uremic toxins can be increased.

2. An apparatus in accordance with claim 1, characterized in that the means for generating a field are configured such that an electromagnetic field is generated having a frequency in the range from 1 MHz to 1 GHz.

3. An apparatus in accordance with claim 1, characterized in that the means for generating a field are configured such that an electromagnetic field is generated having a frequency in the range from 110 to 111 MHz.

4. An apparatus in accordance with claim 1, characterized in that the means for generating a field is configured such that the field has a field strength in the range from up to 4000 V/m.

5. An apparatus in accordance with claim 1, characterized in that the blood treatment apparatus or the element has a curved surface at least regionally; and in that the strip conductors are likewise curved so that they follow the contour of the surface of the blood treatment apparatus or of the element.

6. An apparatus in accordance with claim 1, characterized in that the means extends over the total length of the blood treatment apparatus or of the element or over a part of the total length.

7. An apparatus in accordance with claim 1, further comprising at least one extracorporeal circuit in which the blood treatment apparatus is located.

8. An apparatus in accordance with claim 7, characterized in that the extracorporeal circuit comprises at least one filter which comprises a permeate side and a retentate side, with the blood treatment apparatus or the element being in flow communication with the permeate side.

9. An apparatus in accordance with claim 1, characterized in that the means for generating a field are configured such that an electromagnetic field is generated having a frequency in the range from 1 MHz to 1 GHz.

10. An apparatus in accordance with claim 1, characterized in that the means for generating a field are configured such that an electromagnetic field is generated having a frequency in the range from 50 MHz to 200 MHz.

11. An apparatus in accordance with claim 1, characterized in that the means for generating a field is configured such that the field has a field strength in the range in the range from 2000 V/m to 4000 V/m.

12. An apparatus in accordance with claim 1, characterized in that the means for generating a field is configured such that the field has a field strength in the range from 3000 V/m to 3200 V/m.

13. An apparatus in accordance with claim 1, characterized in that the means extends over more than half the length of the blood treatment apparatus or of the element.

* * * * *